United States Patent [19]

Abe et al.

[11] Patent Number: 4,751,308

[45] Date of Patent: Jun. 14, 1988

[54] PERFLUOROBICYCLOLACTAM COMPOUND AND METHOD FOR PRODUCTION THEREOF

[75] Inventors: Takashi Abe, Kasugai; Eiji Hayashi, Konan; Hiroshige Muramatsu, Nagoya; Hiroshi Okazaki, Munakata; Mahito Soeda, Fukuoka, all of Japan

[73] Assignees: Agency of Industrial Science and Technology; Ministry of International Trade and Industry, both of Tokyo, Japan

[21] Appl. No.: 9,802

[22] Filed: Feb. 2, 1987

[30] Foreign Application Priority Data

Jan. 31, 1986 [JP] Japan .................................. 61-19518

[51] Int. Cl.$^4$ .................. C07D 221/02; C07D 209/02; C07D 209/34
[52] U.S. Cl. .................................... 546/112; 548/452; 548/512
[58] Field of Search ....................... 546/116, 141, 112; 548/452, 512

[56] References Cited

U.S. PATENT DOCUMENTS 3,956,293  5/1976  Pavlik ................................. 544/85

FOREIGN PATENT DOCUMENTS 164772  3/1984  Japan ................................. 546/112

*Primary Examiner*—Alan L. Rotman
*Assistant Examiner*—Robert C. Whittenbaugh
*Attorney, Agent, or Firm*—Oblon, Fisher, Spivak, McClelland & Maier

[57] ABSTRACT

Perfluorobicyclolactam compounds represented by the general formula:

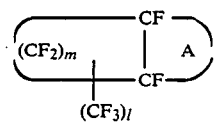

wherein —A— stands for

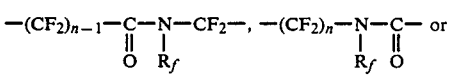

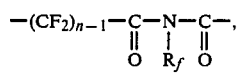

l, m, and n respectively stand for 0 or 1, 3 or 4, and 1 or 2, and $R_f$ stands for a lower perfluoroalkyl group, are novel compounds. These compounds are useful as intermediates for the synthesis of, e.g., functional macromolecular membranes and lubricants. These compounds are produced by subjecting compounds of the general formula:

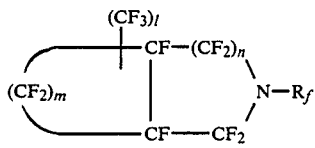

and fuming sulfuric acid to a thermal reaction.

11 Claims, 2 Drawing Sheets

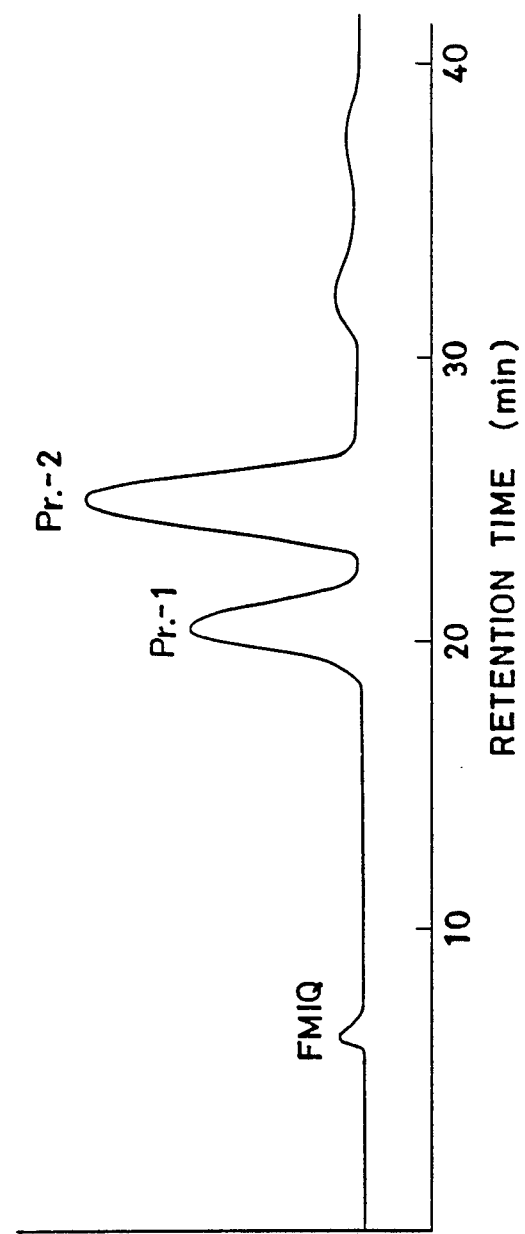

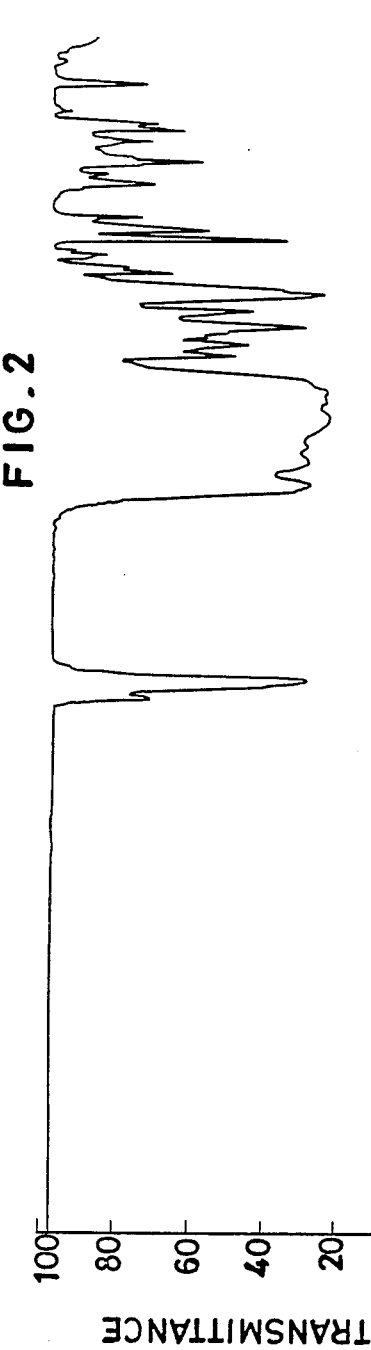
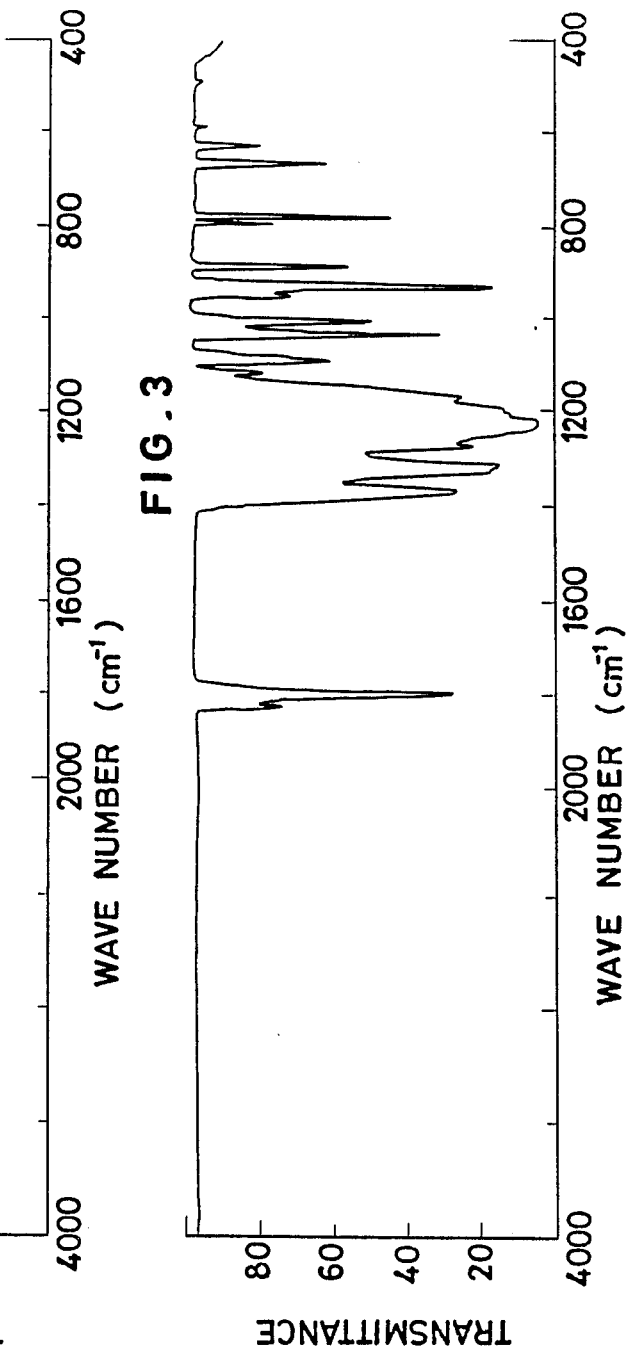

1

PERFLUOROBICYCLOLACTAM COMPOUND AND METHOD FOR PRODUCTION THEREOF

FIELD OF THE INVENTION AND RELATED ART STATEMENT

This invention relates to novel perfluorobicyclolactams useful as intermediates for the synthesis of various useful compounds or substances such as, for example, functional macromolecular membranes and lubricants and to a method for the production of the perfluorobicyclolactams.

In recent years, perfluoro compounds, which are products of the substitution of fluorine atoms for all the hydrogen atoms in compounds, have attracted considerable attention and become the subject of studies in numerous fields involving medicines, agricultural pesticides, and heat media. Perfluoro-compounds of lactams, which contain active carbonyl groups and therefore have potential utility as intermediates for the synthesis of many useful compounds or substances, have, however, drawn very little attention. There are known to the art only perfluoro-(N-methyl-3-oxomorpholine) (U.S. Pat. No. 3,956,293), perfluoro-(N-ethyl-2-oxopyrrolidine) and a few other similar perfluorolactams (Japanese Patent Public Disclosure SHO 59(1984)-164772).

OBJECT AND SUMMARY OF THE INVENTION

An object of this invention is to provide novel perfluorobicyclolactam compounds and a method for the production of these perfluorobicyclolactams.

For achieving this object, this invention provides novel perfluorobicyclolactam compounds represented by the general formula (1):

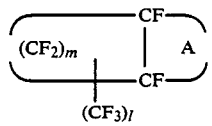

(wherein —A— stands for

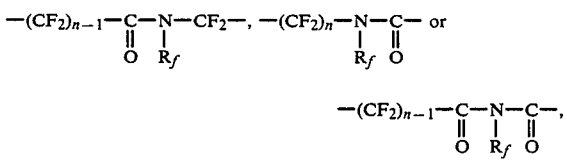

l for 0 or 1, m for 3 or 4, n for 1 or 2, and $R_f$ for a lower perfluoroalkyl group).

This invention further relates to a method for the production of the perfluorobicyclolactam compounds mentioned above by subjecting perfluoro-(N-alkyl-substituted bicycloamine) compounds represented by the formula

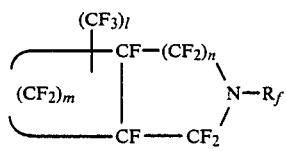

wherein l stands for 0 or 1, m for 3 or 4, n for 1 or 2 and $R_f$ for a lower perfluoroalkyl group and fuming sulfuric acid to a thermal reaction.

BRIEF DESCRIPTION OF THE DRAWINGS

FIG. 1 is a gas chromatogram identifying the product obtained in Example 1 to be a mixture of perfluoro-(3-aza-3-methyl-2-oxobicyclo-[4,4,0]-decane) with perfluoro-(3-aza-3-methyl-4-oxobicyclo-[4,4,0]-decane).

FIG. 2 is an infrared absorption spectrum of perfluoro-(3-aza-3-methyl-2-oxobicyclo-[4,4,0]-decane).

FIG. 3 is an infrared absorption spectrum of perfluoro-(3-aza-3-methyl-4-oxobicyclo-[4,4,0]-decane).

DETAILED DESCRIPTION OF THE PREFERRED EMBODIMENT

The perfluorobicyclolactam compounds of this invention represented by the general formula (1) are characterized by possessing an N-alkyl substituent. As concrete examples of the compounds of this invention, there can be cited such perfluoro-compounds as 3-aza-2-oxobicyclo-[4,4,0]-decane, 3-aza-4-oxobicyclo-[4,4,0]decane, 3-aza-2,4-dioxobicyclo-[4,4,0]-decane, 3-aza-2-oxobicyclo-[4,3,0]-nonane, 3-aza-4-oxobicyclo-[4,3,0]nonane, 3-aza-2,4-dioxobicyclo-[4,3,0]-nonane, 3-aza-2-oxobicyclo-[3,3,0]-octane, and 2-aza-3-oxobicyclo-[3,3,0]octane which have undergone N-substitution with such lower perfluoroalkyls as trifluoromethyl, pentafluoroethyl, perfluoropropyl, and perfluorobutyl groups.

Specifically, preferred perfluorobicyclolactam compounds of the present invention include such bicyclo[4,4,0]-decane lactam derivatives as perfluoro-(3-aza-3-methyl-2-oxobicyclo-[4,4,0]-decane), perfluoro-(3-aza-3-methyl-4-oxobicyclo-[4,4,0]-decane), perfluoro-(3-aza-3-methyl-2,4-dioxobicyclo-[4,4,0]-decane), such bicyclo[4,3,0]-nonane lactam derivatives as perfluoro-(3-aza-3, 8-dimethyl-2-oxobicyclo-[4,3,0]-nonane and perfluoro-(3-aza3,8-dimethyl-4-oxobicyclo-[4,3,0]-nonane), and such bicyclo-[3,3,0]-octane lactam derivatives as perfluoro-(3-aza-3,4,7-trimethyl-2-oxobicyclo-[3,3,0]-octane.

The novel perfluorobicyclolactam compounds of the present invention can be easily identified as by GC analysis and IR analysis.

The novel perfluorobicyclolactam compounds of the present invention are produced by subjecting perfluoro-(N-alkyl-substituted bicycloamine) compounds represented by the formula:

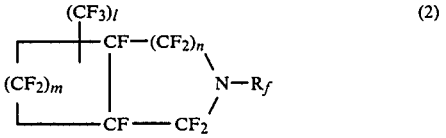

(wherein l stands for 0 or 1, m for 3 or 4, n for 1 or 2, and $R_f$ for a lower perfluoroalkyl group) and fuming sulfuric acid to a thermal reaction.

The compounds of the aforementioned formula (2) which are raw materials for the production of the compounds of this invention can be produced by fluorinating the corresponding hydrogen containing compounds such as, for example, N-alkyldecahydroisoquinolines by any of the methods known to the art such as, for example, the direct fluorination method, the electrochemical fluorination method, and the cobalt trifluoride fluorination method. When an N-alkyldecahydroisoquinoline is fluorinated electrochemically, there are produced a corresponding perfluoro-N-alkyldecahydroisoquinoline plus such condensed ring isomers as those of the formulas (3) and (4):

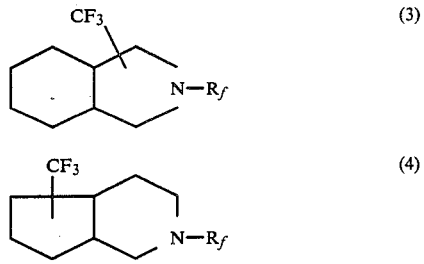

This mixture containing these condensed ring isomers may be used directly, i.e. in the state not deprived of these isomers, in working the method of the present invention.

The sulfuric acid to be used in the thermal reaction is a fuming sulfuric acid of a concentration of 10 to 60% by weight. As regards the conditions for the aforementioned reaction of perfluoro-(N-alkyl-substituted bicycloamine) compound and fuming sulfuric acid, the mol ratio of $SO_3$/perfluoro-(N-alkyl-substituted bicycloamine) is in the range of 1 to 10, preferably 3 to 6, the reaction temperature is in the range of 100° to 200° C., preferably 140° to 170° C., and the reaction time is in the range of 1 to 100 hours, preferably 20 to 50 hours.

If the molar ratio is smaller than 1, the conversion is not sufficiently high. If the molar ratio exceeds 10, the yield is clearly insufficient. If the reaction temperature does not reach 100° C., the time required for completing the reaction is very long. If the temperature exceeds 200° C., the reaction entails secondary reactions heavily and the yield of the lactam derivative aimed at is poor.

If the reaction time is shorter, the reaction does not proceed to completion. If the reaction time is too long, the yield of the product aimed at is lowered because of heavy secondary reactions.

This reaction system may incorporate therein a catalytic amount of mercuric sulfate or molybdenum pentachloride so as to improve the yield of a perfluorobicyclolactam aimed at by the reaction.

Specifically, the amount of this catalyst to be incorporated suitably falls in the range of 0.01 to 0.02 g per g of perfluoroamine.

The incorporation of the catalyst enhances the yield by about 0 to 5%.

After the reaction carried out by the method of this invention is completed, separation of the perfluorobicyclolactam compound from the reaction mixture can be effected by any of the known techniques. One example of such techniques is shown below. First, sulfuric acid is removed from the reaction product. Then, the unaltered perfluoro-(N-alkyl-substituted bicycloamines) and the perfluorobicyclolactam compound aimed at by the reaction are separated from each other by a suitable treatment such as, for example, distillation or gas chromatography. Where the reaction mixture spontaneously separates into an upper layer containing mainly the unaltered raw material and the reaction product aimed at and a lower sulfuric acid layer, the upper and lower layers are in situ separated from each other. The reaction product aimed at and the unaltered raw material dissolved in the sulfuric acid layer are desirably extracted by a chlorofluorocarbon type solvent such as, for example, perfluoroamine, perfluoroether, perfluorocarbon, or 1,1,2-trichlorotrifluoroethane. When the reaction mixture does not separate into the upper layer and the lower layer of sulfuric acid, it is desirable to extract the reaction product aimed at and the unaltered raw material from the reaction mixture with the aid of the aforementioned chlorofluorocarbon type solvent.

The perfluorobicyclolactam compounds of the present invention not only are novel compounds but also are useful intermediates for the synthesis of various useful compounds and substances such as functional macromolecular films and lubricants. These novel perfluorobicyclolactam compounds can be produced by the method of the present invention.

Now, a typical procedure used for the production of a functional macromolecular compound from perfluoro-(3-aza-3-methyl-2-oxobicyclo-[4,4,0]-decane), a species of the perfluorobicyclolactam of the present invention, will be described below by way of illustration.

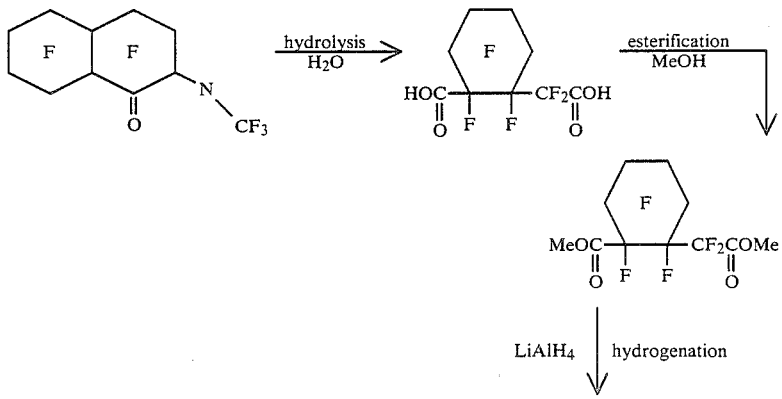

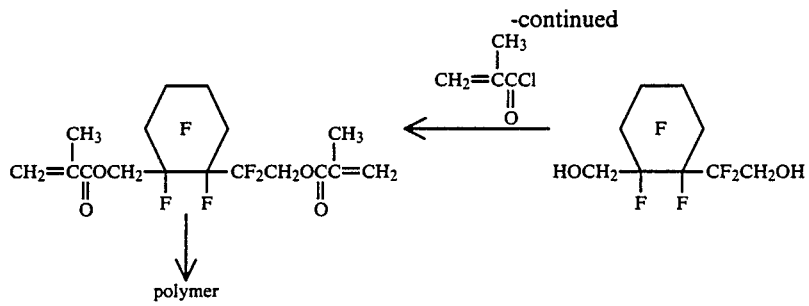

EXAMPLES 1-4

Ampoules made of Pyrex glass 15 mm in inside diameter were charged with perfluoro-(N-methyldecahydroisoquinoline) (FMIQ) and 30% fuming sulfuric acid (30%f-SA) in the different ratios indicated in Table 1 and further charged with a catalytic amount of MoCl$_5$ (with the use of MoCl$_5$ omitted in Example 4). The ampoules were then sealed while being cooled with ice, set in position in an electric furnace kept at the different temperatures indicated in Table 1, and left standing for a total period of 24 hours with brief shaking at intervals of 1 to 2 hours, for the purpose of reaction.

After the reaction was completed, the ampoule was left standing to cool, and then further cooled with liquefied nitrogen, and opened. The reaction mixture spontaneously separated into two layers and the reaction product aimed at was obtained as an upper layer.

The reaction products of Examples 1-4 were found by GC analysis and IR analysis to comprise perfluoro-(3-aza3-methyl-2-oxobicyclo-[4,4,0]-decane) (Pr.-1) and perfluoro-(3-aza-3-methyl-4-oxobicyclo-[4,4,0]-decane) (Pr.-2) as intended. The yields of Pr.-1 and Pr.-2 as products and the conversion of FMIQ as the raw material were as shown in Table 1.

with a catalytic amount of MoCl$_5$, hermetically sealed, and left standing, with shaking carried out briefly at intervals of 1 to 2 hours, for a total period of 24 hours for the purpose of reaction.

After the reaction was completed, the reaction product was obtained by subjecting the reaction mixture to extraction with a chlorofluorocarbon type solvent. The reaction products were subjected to GC analysis and IR analysis. The yields of Pr.-1, Pr.-2, perfluoro-(trans-3-aza-3-methyl-2,4-dioxobicyclo-[4,4,0]-decane) (Pr.-3), and perfluoro-(cis-3-aza-3-methyl-2,4-dioxobicyclo-[4,4,0]decane) (Pr.-4) as the target products and the conversion of FMIQ as the raw material were as shown in Table 2.

As the result of IR analysis, the reaction products were found to have positions of absorption by the carbonyl group as follows.

Pr.-1: 1,823cm$^{-1}$, 1,797cm$^{-1}$(s)

Pr.-2: 1,820cm$^{-1}$, 1,783cm$^{-1}$(s)

Pr.-3: 1,819cm$^{-1}$, 1,782cm$^{-1}$(s)

Pr.-4: 1,856cm$^{-1}$, 1,795cm$^{-1}$(s)

TABLE 1

| Example No. | Amounts of FMIQ used (g) | Amount of 30% f-SA used (g) | Molar ratio | Amounts of MoCl$_5$ added (g) | Reaction temperature (°C.) | Yield (mol %) Pr.-1 | Yield (mol %) Pr.-2 | Conversion of FMIQ (wt %) |
|---|---|---|---|---|---|---|---|---|
| 1 | 1.90 | 3.0 | 2.9 | 0.02 | 160 | 14.9 | 27.2 | 98.6 |
| 2 | 1.93 | 5.0 | 4.8 | 0.02 | 160 | 10.7 | 23.8 | 99.6 |
| 3 | 1.86 | 3.0 | 3.0 | 0.02 | 150 | 16.0 | 20.7 | 54.1 |
| 4 | 1.83 | 5.0 | 5.1 | 0 | 150 | 20.8 | 31.8 | 83.2 |

TABLE 2

| Example No. | Amount of FMIQ used (g) | Amount of 30% f-SA used (g) | Molar ratio | Amount of MoCl$_5$ added (g) | Reaction temperature (°C.) | Reaction time (hrs) | Yield (mol %) Pr.-1 | Pr.-2 | Pr.-3 | Pr.-4 | Conversion of FMIQ (wt %) |
|---|---|---|---|---|---|---|---|---|---|---|---|
| 5 | 58.2 | 94.2 | 3.0 | 0.5 | 160 | 24 | 5.3 | 6.2 | | | 18.4 |
| 6 | 58.0 | 95.0 | 3.0 | 0.5 | 170 | 24 | 3.6 | 6.7 | | | 22.5 |
| 7 | 50.2 | 91.0 | 3.4 | 0.5 | 170 | 48 | 17.8 | 27.8 | 8.5 | 5.8 | 93.8 |

The gas chromatogram and the infrared absorption spectra which served to identify the products of Example 1 are shown respectively in FIG. 1 and FIGS. 2 and 3. FIG. 1 is the gas chromatogram of a crude product (liquid phase: Silicone DC QF-1).

EXAMPLES 5-7

Reaction vessels made of Monel metal were charged with perfluoro-(N-methyldecahydroisoquinoline) (FMIQ) and 30% fuming sulfuric acid (30%f-SA) in the different ratios indicated in Table 2, further charged

EXAMPLE 8

An ampoule made of Pyrex glass 15 mm in inside diameter was charged with 1.82 g of perfluoro-(3-aza-3-methyl-8-methylbicyclo-[4,3,0]-nonane) and 5.0 g of 30% fuming sulfuric acid and further charged with 0.02 g of MoCl$_5$. The ampoule was then sealed while being kept cooled with ice, set in position in an electric furnace kept at 160° C., and left standing with shaking carried out briefly at intervals of 1 to 2 hours, for a total period of 24 hours for the purpose of reaction.

After the reaction was completed, the ampoule was left cooling, and further cooled with liquefied nitrogen, and opened. The reaction product was obtained by selectively removing the upper layer when the reaction mixture spontaneously separated into two layers.

The reaction product was found to comprise perfluoro-(3-aza-3-methyl-8-methyl-2-oxobicyclo-[4,3,0]nonane) (Pr.-5) and perfluoro-(3-aza-3-methyl-8-methyl-4-oxobicyclo-[4,3,0]-nonane) (Pr.-6). The yields of Pr.-5 and Pr.-6 were 23.7% and 26.9% respectively and the conversion of the raw material was 94.8%.

EXAMPLE 9

A reaction vessel made of Monel metal was charged with 51.5 g of perfluoro-(3-aza-3-methyl-8-methylbicyclo[4,3,0]-nonane) and 103.5 g of 30% fuming sulfuric acid and further charged with 0.5 g of MoCl$_5$, hermetically sealed, and left standing at 170° C. for 48 hours for the purpose of reaction.

After the reaction was completed, the reaction product was obtained by extraction with a chlorofluorocarbon type solvent.

The reaction product was found to comprise Pr.-5 and Pr.-6. The yields of the products were 22.5% and 24.5% respectively. The conversion of the raw material was 91.0%.

As the result of IR analysis, they were found to have positions of absorption by the carbonyl group as follows.

Pr.-5: 1,816cm$^{-1}$, 1,784cm$^{-1}$(s)
Pr.-6: 1,873cm$^{-1}$, 1,793cm$^{-1}$(s)

What is claimed is:

1. A perfluorobicyclolactam compound represented by the formula:

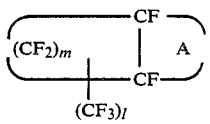

(wherein —A— stands for one member selected from the group consisting of

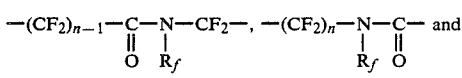

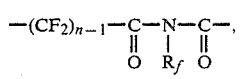

l for 0 or 1, m for 3 or 4, n for 1 or 2, and R$_f$ for a lower perfluoroalkyl group).

2. The perfluorobicyclolactam compound of claim 1, wherein —A— is

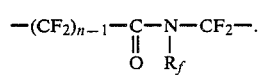

3. The perfluorobicyclolactam compound of claim 1, wherein —A— is

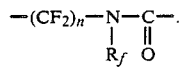

4. The perfluorobicyclolactam compound of claim 1, wherein —A— is

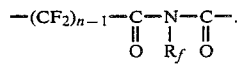

5. The perfluorobicyclolactam compound of claim 1, wherein said lower perfluoroalkyl group is one member selected from the class consisting of trifluoromethyl group, pentafluoroethyl group, perfluoropropyl group, and perfluorobutyl group.

6. A method for the production of a perfluorobicyclolactam compound represented by the formula:

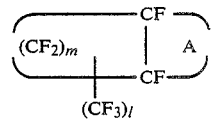

wherein —A— stands for one member selected from the group consisting of

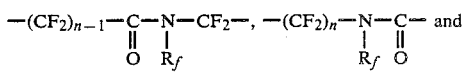

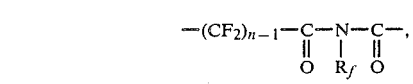

l for 0 or 1, m for 3 or 4, n for 1 or 2, and R$_f$ for a lower perfluoroalkyl group, which comprises subjecting a perfluoro-(N-alkyl-substituted bicycloamine) compound represented by the formula:

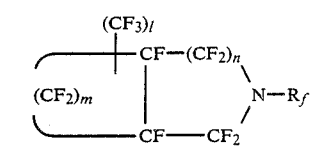

wherein l, m, n, and R$_f$ have the same meanings as defined above and fuming sulfuric acid to a thermal reaction.

7. The method of claim 6, wherein —A— is

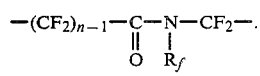

8. The method of claim 6, wherein —A— is

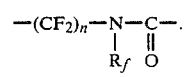

9. The method of claim 6, wherein —A— is

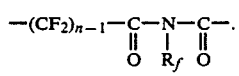

10. The method of claim 6, wherein said lower perfluoralkyl group is one member selected from the class consisting of trifluoromethyl group, pentafluoroethyl group, perfluoropropyl group, and perfluorobutyl group.

11. The method of claim 6, wherein said thermal reaction is carried out under the conditions wherein the molar ratio of perfluoro-(N-alkyl-substituted bicycloamine) compound to fuming sulfuric acid of a concentration of 10 to 60 wt %, i.e. $SO_3$/perfluoro-(N-alkyl substituted bicycloamine), is in the range of 1 to 10, the reaction temperature is in the range of 100° to 200° C., and the reaction time is in the range of 1 to 100 hours.

* * * * *